(12) United States Patent
Lensing (10) Patent No.: US 6,537,833 B1
(45) Date of Patent: *Mar. 25, 2003

(54) METHOD AND APPARATUS FOR CHARACTERIZING AN INTERCONNECT STRUCTURE PROFILE USING SCATTEROMETRY MEASUREMENTS

(75) Inventor: Kevin R. Lensing, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/885,411

(22) Filed: Jun. 19, 2001

(51) Int. Cl.$^7$ .............................................. H01L 21/66
(52) U.S. Cl. ........................................... 438/14; 438/15
(58) Field of Search ............................. 438/14, 15, 16; 356/351, 445

(56) References Cited

U.S. PATENT DOCUMENTS

| | | | | |
|---|---|---|---|---|
| 5,355,306 A | * | 10/1994 | Waldo, III | 250/491.1 |
| 5,393,624 A | | 2/1995 | Ushijima | 430/30 |
| 5,867,276 A | | 2/1999 | McNeil et al. | 356/445 |
| 5,880,838 A | | 3/1999 | Marx et al. | 356/351 |
| 5,889,593 A | * | 3/1999 | Bareket | 356/445 |
| 5,905,573 A | * | 5/1999 | Stallard et al. | 356/519 |
| 5,923,423 A | * | 7/1999 | Sawatari et al. | 356/237.5 |
| 5,955,654 A | * | 9/1999 | Stover et al. | 73/1.89 |
| 5,963,329 A | * | 10/1999 | Conrad et al. | 356/613 |
| 6,051,348 A | | 4/2000 | Marinaro et al. | 430/30 |
| 6,245,584 B1 | | 6/2001 | Marinaro et al. | 438/14 |
| 6,259,521 B1 | * | 7/2001 | Miller et al. | 356/237.5 |
| 6,292,265 B1 | * | 9/2001 | Finarov et al. | 250/559.27 |
| 6,383,824 B1 | * | 5/2002 | Lensing | 356/445 |
| 6,383,888 B1 | * | 5/2002 | Stirton | 430/22 |
| 6,388,253 B1 | * | 5/2002 | Su | 250/252.1 |

OTHER PUBLICATIONS

Bishop et al., "Use of Scatterometry for resist process control," *SPIE Integrated Circuit Metrology, Inspection and Process Control,* 1673:441–452, 1992.

Hickman et al., "Use of diffracted light from latent images to improve lithography control," *SPIE Integrated Circuit Metrology, Inspection and Process Control,* 1464:245–257, 1991.

McNeil et al., "Scatterometry applied to microelectronics processing—Part 1," *Solid State Technology,* 37(3):29–56, 1993.

Miller and Mellicamp, "Development of an end–point detection procedure for the post–exposure bake process," *Integrated circuit metrology, inspection, and process control IX:* 20–22, Feb., 1995, Santa Clara, California, *SPIE Integrated Circuit Metrology, Inspection and Process Control,* 2439:78–88, 1995.

(List continued on next page.)

Primary Examiner—John F. Niebling
Assistant Examiner—Olivia Luk
(74) Attorney, Agent, or Firm—Williams, Morgan & Amerson (57) ABSTRACT

A method for characterizing an interconnect structure profile includes providing a wafer having a grating structure including a plurality of interconnect structures; illuminating at least a portion of the grating structure; measuring light reflected from the grating structure to generate a reflection profile; and determining a profile of the interconnect structures based on the reflection profile. A metrology tool adapted to receive a wafer having a grating structure including a plurality of interconnect structures includes a light source, a detector, and a data processing unit. The light source is adapted to illuminate at least a portion of the grating structure. The detector is adapted to measure light reflected from the grating structure to generate a reflection profile. The data processing unit is adapted to determine a profile of the interconnect structures based on the reflection profile.

53 Claims, 5 Drawing Sheets

OTHER PUBLICATIONS

Milner et al., "Latent image exposure monitor using scatterometry," *SPIE Integrated Circuit Metrology, Inspection and Process Control*, 1673:274–283, 1992.

Prins et al., "Scatterometric sensor for PEB process control," *Metrology, inspection, and process control for microlithography*, X:Mar. 11–13, 1996, Santa Clara, California, *SPIE Integrated Circuit Metrology, Inspection and Process Control*,2725:710–719, 1996.

Raymond et al., "Multiparameter process metrology using scatterometry," In: *Optical characterization techniques for high–performance microelectronic device manufacturing II, SPIE—The International Society for Optical Engineering*, 2638:84–93, Austin, Texas, Oct. 25–26, 1995.

Raymond et al., "Scatterometric sensor for lithography," In: *Manufacturing process control for microlectronic devices and circuits, SPIE—The International Society for Optical Engineering*, 2336:37–49, Austin, Texas, Oct. 20–21, 1994.

Sturtevant et al., "Post–exposure bake as a process–control parameter for chemically–amplified photoresist," *Metrology, inspection, and process control for microlithography*, VII, Mar. 2–4, 1993, Santa Jose, California, *SPIE Integrated Circuit Metrology, Inspection and Process Control*, vol. 1926, 1993.

Sturtevant et al., "Use of scatterometric latent image detector in closed loop feedback control of linewidth," *SPIE Integrated Circuit Metrology, Inspection and Process Control*, 2196:352–359, 1994.

* cited by examiner

METHOD AND APPARATUS FOR CHARACTERIZING AN INTERCONNECT STRUCTURE PROFILE USING SCATTEROMETRY MEASUREMENTS

BACKGROUND OF THE INVENTION

1. Field of the Invention

This invention relates generally to the field of semiconductor device manufacturing and, more particularly, to a method and apparatus for characterizing an interconnect structure profile using scatterometry measurements.

2. Description of the Related Art

There is a constant drive within the semiconductor industry to increase the quality, reliability and throughput of integrated circuit devices, e.g., microprocessors, memory devices, and the like. This drive is fueled by consumer demands for higher quality computers and electronic devices that operate more reliably. These demands have resulted in a continual improvement in the manufacture of semiconductor devices, e.g., transistors, as well as in the manufacture of integrated circuit devices incorporating such transistors. Additionally, reducing the defects in the manufacture of the components of a typical transistor also lowers the overall cost per transistor as well as the cost of integrated circuit devices incorporating such transistors.

The technologies underlying semiconductor processing tools have attracted increased attention over the last several years, resulting in substantial refinements. However, despite the advances made in this area, many of the processing tools that are currently commercially available suffer certain deficiencies. In particular, such tools often lack advanced process data monitoring capabilities, such as the ability to provide historical parametric data in a user-friendly format, as well as event logging, real-time graphical display of both current processing parameters and the processing parameters of the entire run, and remote, i.e., local site and worldwide, monitoring. These deficiencies can engender nonoptimal control of critical processing parameters, such as throughput, accuracy, stability and repeatability, processing temperatures, mechanical tool parameters, and the like. This variability manifests itself as within-run disparities, run-to-run disparities and tool-to-tool disparities that can propagate into deviations in product quality and performance, whereas an ideal monitoring and diagnostics system for such tools would provide a means of monitoring this variability, as well as providing means for optimizing control of critical parameters.

Semiconductor devices are manufactured from wafers of a substrate material. Layers of materials are added, removed, and/or treated during fabrication to create the electrical circuits that make up the device. The fabrication essentially comprises four basic operations. Although there are only four basic operations, they can be combined in hundreds of different ways, depending upon the particular fabrication process.

The four operations typically used in the manufacture of semiconductor devices are:

- layering, or adding thin layers of various materials to a wafer from which a semiconductor device is produced;
- patterning, or removing selected portions of added layers;
- doping, or placing specific amounts of dopants in the wafer surface through openings in the added layers; and
- heat treatment, or heating and cooling the materials to produce desired effects in the processed wafer.

Occasionally, during the fabrication process, one or more process steps are not performed properly on a production wafer. Such processing faults may be due to an error in the fabrication facility automated work flow system (e.g., a database or control script error), a tool failure, or an operator error. If the faulty process steps occur early during the fabrication process, it is not uncommon for the faulty wafer to undergo many subsequent steps prior to the faulty fabrication being identified. Often such identification occurs much further down the processing line, such as during the performance of electrical tests on the devices formed on the wafer or by periodic destructive cross-sectional examination techniques. As a result, many resources, such as materials, tool time, operator time, etc., are wasted until the faulty fabrication can be identified.

One particular processing situation where fault detection is difficult involves the etching of metal interconnect lines (e.g., aluminum). The interconnect lines typically include a stack of various layers, including an antireflective coating (ARC) layer disposed over the aluminum layer and a hard mask layer (e.g., silicon dioxide) formed over the ARC layer. A more detailed description of an interconnect structure is provided below in reference to FIGS. 2A–2C. Generally, an anisotropic sputter etch technique is used to etch the hard mask and ARC layer, followed by an isotropic chemical process that etches the interconnect lines. Because the aluminum layer is not readily susceptible to sputter etching techniques, reactive gases are added to the plasma after the ARC layer is etched. The aluminum etch process is driven by chemical reaction and is therefore isotropic in nature. The lateral component of the isotropic etch can result in undercutting or scalloping of the metal layer, which reduces current carrying volume of the interconnect line and leaves the device subject to shorts or heat-related failures. This aluminum undercut and resultant reduction in current carrying volume is typically not detected until electrical tests are performed near the end of the fabrication process, where device failures are detected.

Current techniques for evaluating the width of interconnect structures involve taking a top down, one-dimensional measurement of the interconnect line using a scanning electron microscope. Effectively, this technique measures the width of the top layer of the stack (i.e., the hard mask layer and/or ARC layer). This one dimensional width measurement cannot identify any undercutting of the metal layer.

The present invention is directed to overcoming, or at least reducing the effects of, one or more of the problems set forth above.

SUMMARY OF THE INVENTION

One aspect of the present invention is seen in a method for characterizing an interconnect structure profile. The method includes providing a wafer having a grating structure including a plurality of interconnect structures; illuminating at least a portion of the grating structure; measuring light reflected from the grating structure to generate a reflection profile; and determining a profile of the interconnect structures based on the reflection profile.

Another aspect of the present invention is seen in a metrology tool adapted to receive a wafer having a grating structure including a plurality of interconnect structures. The metrology tool includes a light source, a detector, and a data processing unit. The light source is adapted to illuminate at least a portion of the grating structure. The detector is adapted to measure light reflected from the grating structure to generate a reflection profile. The data processing unit is adapted to determine a profile of the interconnect structures based on the reflection profile.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
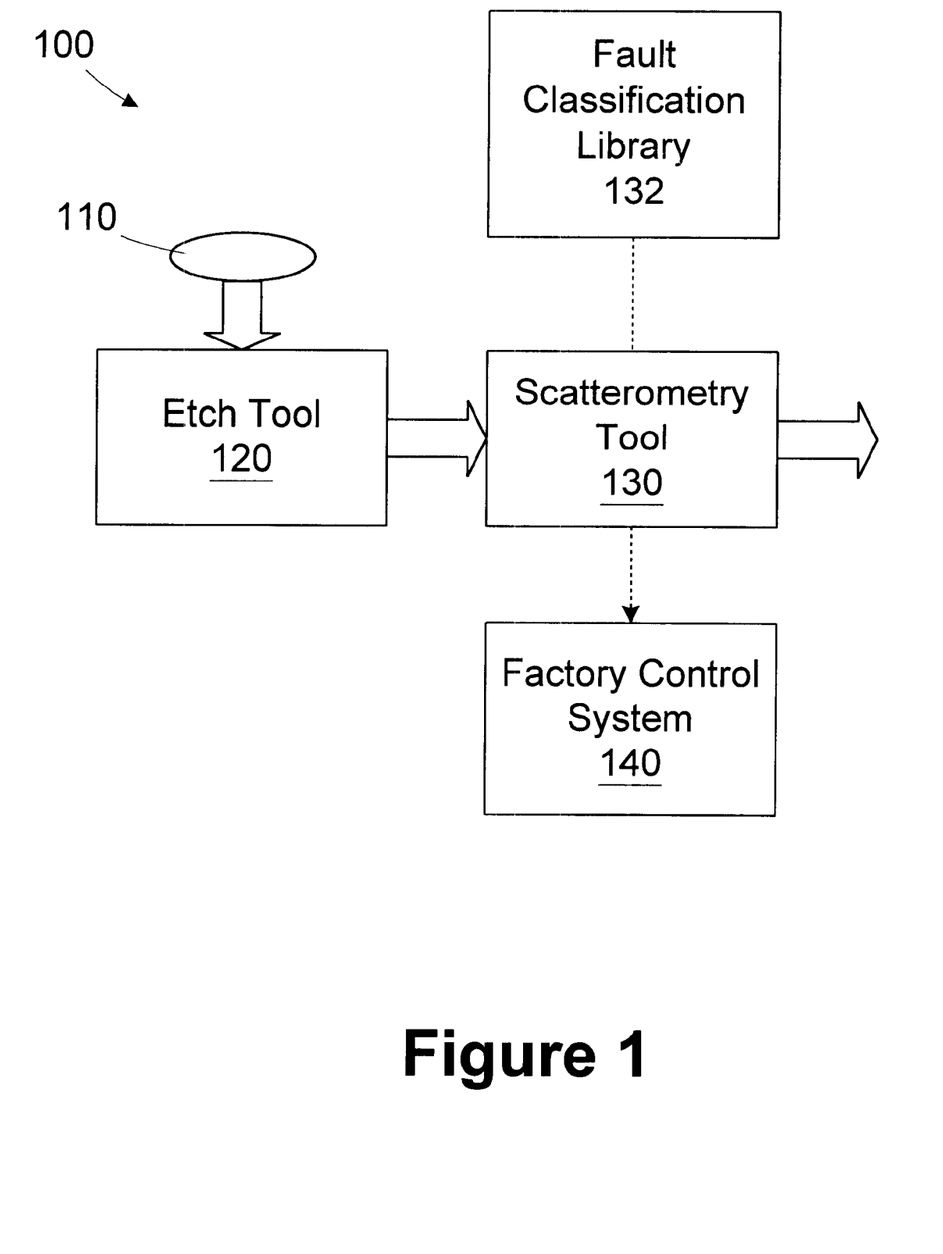
FIG. 1 is a simplified diagram of an illustrative processing line for processing wafers in accordance with one illustrative embodiment of the present invention.

Referring now to the Figures, and particularly to FIG. 1, a simplified block diagram of a processing line 100 useful for processing wafers 110 is provided. The processing line 100 includes an etch tool 120 for forming features on the wafer 110, such as interconnect features. A scatterometry tool 130 is provided for detecting faults in the features formed by the etch tool 120.

The operation of the scatterometry tool 130 is described in greater detail below. In general, the scatterometry tool 130 includes optical hardware, such as an ellipsometer or reflectometer, and a data processing unit loaded with a scatterometry software application for processing data collected by the optical hardware. For example, the optical hardware may include a model OP5230 or OP5240 with a spectroscopic ellipsometer offered by Therma-Wave, Inc. of Freemont Calif. The data processing unit may comprise a profile application server manufactured by Timbre Technologies, a subsidiary of Tokyo Electron Limited, Inc. of Kumamoto, Japan and distributed by Therma-Wave, Inc.

In general, the scatterometry tool 130 measures features formed on the wafer 110 by measuring light reflected from a grating structure, such as a group of interconnect structures, and comparing the measured reflection profile to a fault classification library 132 of reflection profiles to characterize the profile of the interconnect structures and identify corresponding processing faults. The fault classification library 132 includes a library of reflection profiles associated with known processing faults for the interconnect structures. Reference scatterometry libraries are commercially available from Timbre Technologies, Inc.

Figure 2A:
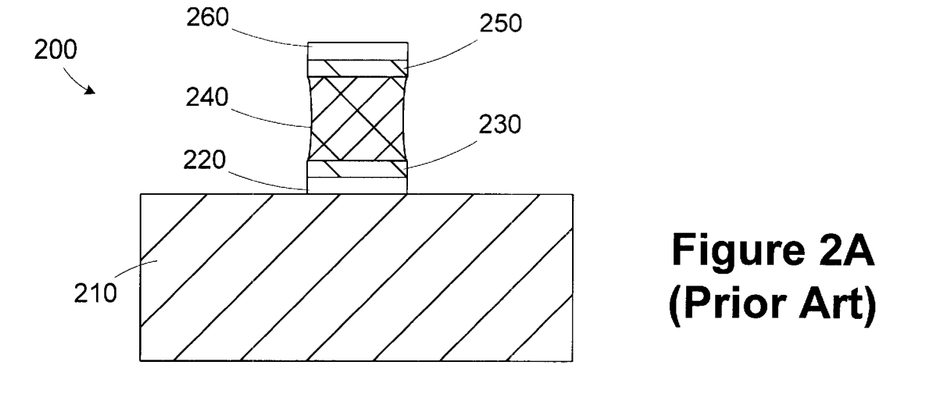
FIGS. 2A, 2B, and 2C are cross section views of exemplary semiconductor devices.

Referring to FIG. 2A, a cross-section view of an interconnect structure 200 is provided. The interconnect structure 200 of FIG. 2A represents an expected configuration for the features formed by the etch tool 120. The interconnect structure 200 is formed over an interlayer dielectric (ILD) layer 210, such as silicon dioxide. In the illustrated embodiment, the interconnect structure 200 includes a first barrier layer 220, a second barrier layer 230, a metal layer 240, an antireflective coating (ARC) layer 250, and a hard mask layer 260. In the illustrated embodiment, the first barrier layer 220 is titanium, and the second barrier layer 230 and ARC layer 250 are titanium nitride. The hard mask layer 260 is silicon dioxide, and the metal layer 240 is aluminum. The illustrated configuration is exemplary. Other configurations including differing materials and numbers of layers may also be used.

The various layers 220, 230, 240, 250, 260 are deposited to form a film stack. The hard mask layer 260 is patterned to form an interconnect layout. One or more etching processes that do not etch the hard mask layer 260 are used by the etch tool 120 to form the interconnect structure 200 from the film stack. The interconnect etching processes include an anisotropic component and an isotropic component. The layers 220, 230, 250 are primarily etched by the anisotropic component. The isotropic component (ie., chemical etch) is typically necessary because the metal layer 240 does not readily etch using a physical anisotropic etch process.

An exemplary etch process for forming the interconnect structure 200 includes a timed etch using a gas mixture of argon and boron trichloride ($BCl_3$) to pattern the hard mask layer 260. A second timed etch using argon, boron trichloride, and chlorine ($Cl_2$) reactant gases is used to etch the ARC layer 250. A first endpointed etch (e.g., based on atomic emission spectra) using argon, boron trichloride, and a higher ratio of chlorine is used to etch the metal layer 240. The chlorine provides the isotropic component necessary to effectively etch the metal layer 240. A second endpointed overetch is used to clear any remaining portions of the metal layer 240 and the first and second barrier layers 220, 230. The overetch may be endpointed by identifying an oxide peak in the atomic emission spectra, indicating exposure of the ILD layer 210. The isotropic component of the etch processes used to form the interconnect structure result in the metal layer 240 having a slightly concave profile (i.e., also referred to as an undercut profile.

Figure 2B:
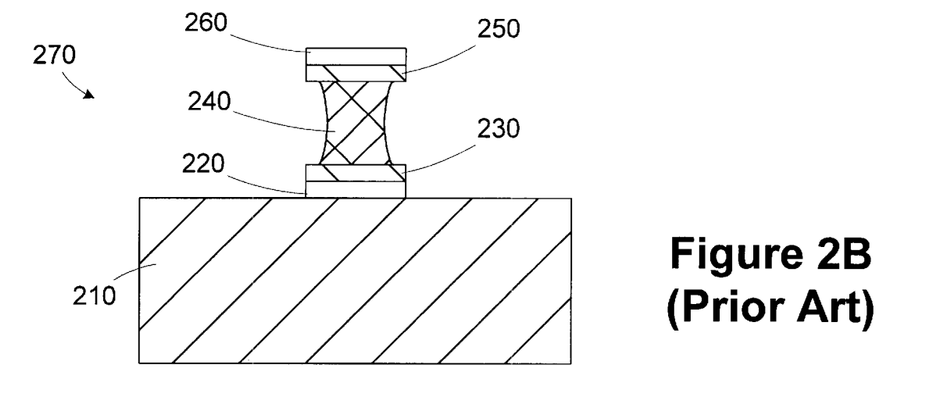

FIG. 2B illustrates a cross-section view of a misprocessed interconnect structure 270, wherein the metal layer 240 has a severe degree of undercutting. Undercutting may be caused by variations or problems with the etch process parameters that result in the isotropic component of the etch rate being too high relative to the anisotropic component. The high level of undercutting degrades the performance characteristics of the interconnect structure 270, and thus, compromises the operation of the completed device. The ARC layer 250 and hard mask layer 260 prevent the detection of the undercutting of the metal layer 240 by a top-down width measurement technique.

Figure 2C:
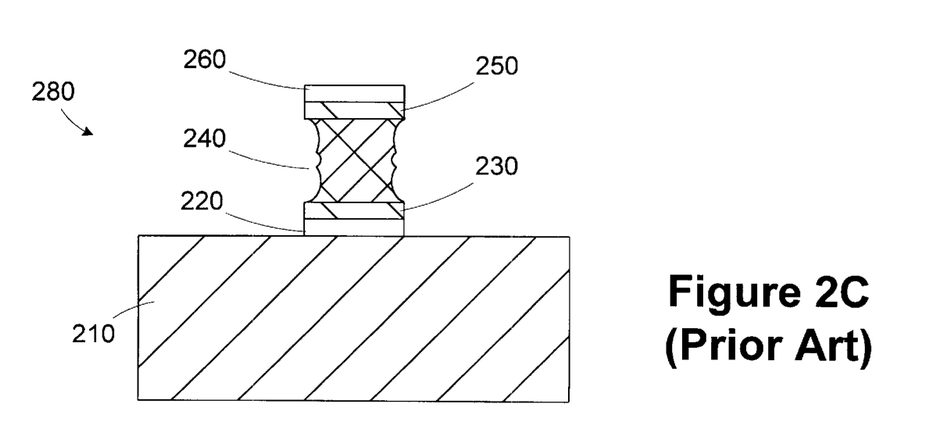

FIG. 2C illustrates a cross-section view of a misprocessed interconnect structure 280, wherein the metal layer 240 has a scalloped profile. Scalloping may be caused by improper etch conditions, such as bias power, pressure, etc. A severely scalloped profile may also degrade the performance characteristics of the interconnect structure 280 and compromise the operation of the completed device. The ARC layer 250 and hard mask layer 260 also prevent the detection of the scalloped condition of the metal layer 240 by a top-down width measurement technique.

Figure 3:
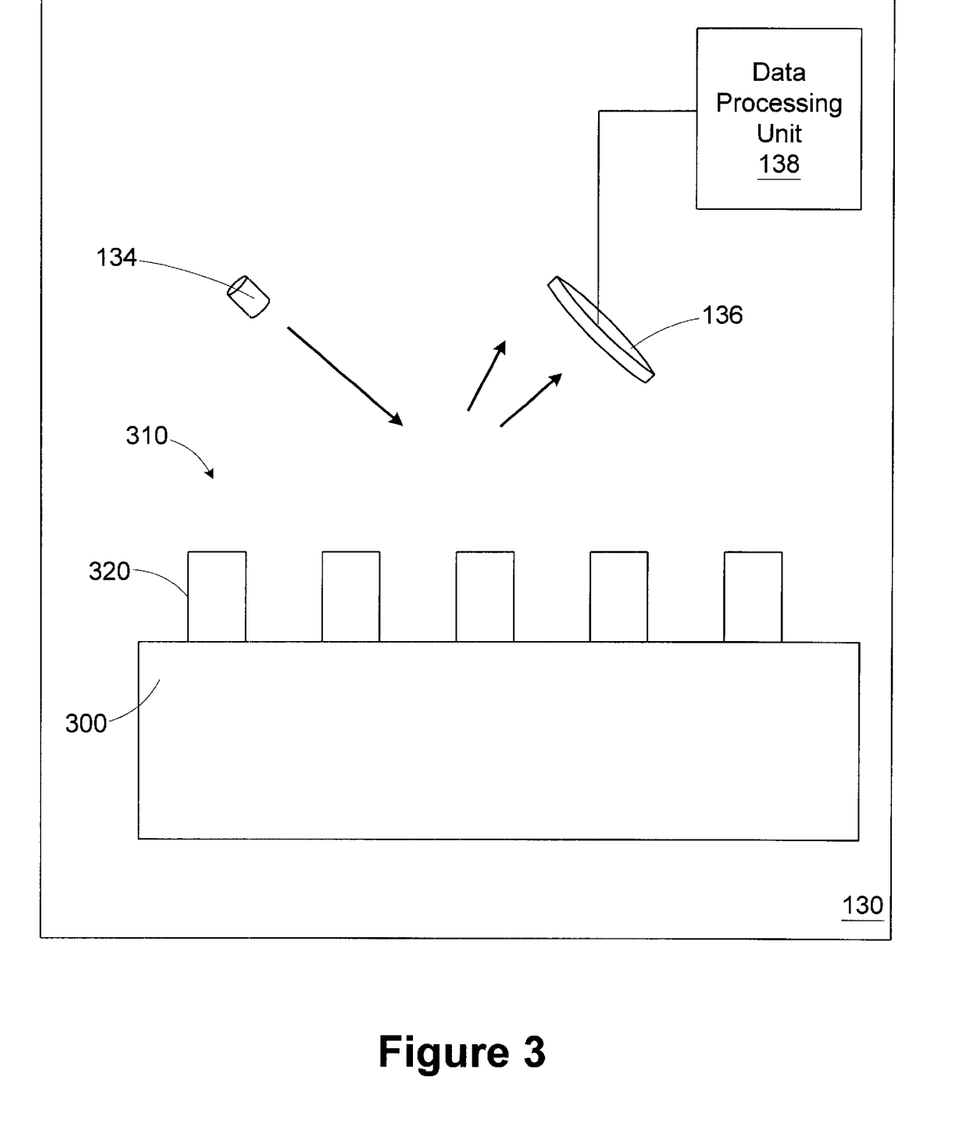
FIG. 3 is a simplified view of the scatterometry tool of FIG. 1 loaded with a wafer including a grating structure.

The operation of the scatterometry tool is now described in greater detail with reference to FIG. 3. For purposes of illustration, the operation of the scatterometry tool is described as it may be applied to measuring characteristics of the interconnect structures 200, 270, 280 shown in FIGS. 2A, 2b, and 2C. The scatterometry tool 130 is loaded with a wafer 300 having a grating structure 310 comprising a plurality of interconnect structures 320. The grating structure 310 may be features formed in a production device on the wafer 300, or alternatively, the grating structure 310 may be a test structure having dimensions and construction materials similar to a production device. The scatterometry tool 130, includes a light source 134 and a detector 136 positioned proximate the grating structure 310. The light source 134 of the scatterometry tool 130 illuminates at least a portion of the grating structure 310, and the detector 136 takes optical measurements, such as intensity or phase, of the reflected light. A data processing unit 138 receives the optical measurements from the detector 134 and processes the data to determine a profile of the interconnect structures 320 and identify a processing fault therewith.

Although the invention is described using a scatterometry tool 130 designed to measure reflected light intensity or phase, other measurement tools, such as an ellipsometer, a reflectometer, a spectrometer, or some other light measuring device may be used. The scatterometry tool 130 may use monochromatic light, white light, or some other wavelength or combinations of wavelengths, depending on the specific implementation. The angle of incidence of the light may also vary, depending on the specific implementation. The light analyzed by the scatterometry tool 130 typically includes a reflected component (i.e., incident angle equals reflected angle) and a refracted component (i.e., incident angle does not equal the reflected angle). For purposes of discussion here, the term "reflected" light is meant to encompass both components.

Variations in the characteristics of the grating structure 310 cause changes in the reflection profile (e.g., intensity vs. wavelength—$\tan(\delta)$, phase vs. wavelength—$\sin(\psi)$, where $\delta$ and $\psi$ are common scatterometry outputs known to those of ordinary skill in the art) measured by the scatterometry tool 130. The particular reflection profile expected for any structure depends on the specific geometry of the grating structure 310 and the parameters of the measurement technique employed by the scatterometry tool 130 (e.g., light bandwidth, angle of incidence, etc.). The profiles in the fault classification library 132 are typically calculated theoretically by employing Maxwell's equations based on the topology and geometry of the grating structure 310. For example, the reflection profile for a scalloped interconnect feature may be approximated by modeling a series of stacked metal trapezoids of different dimensions. The profiles in the fault classification library 132 may also be generated empirically by measuring reflection profiles of sample wafers and subsequently characterizing step the measured wafers by some other destructive or non-destructive examination technique.

Figure 4A:
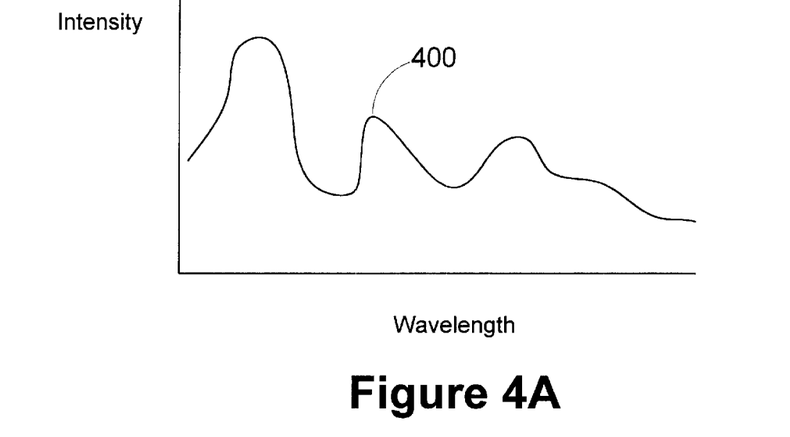
FIGS. 4A, 4B, and 4C illustrate exemplary scatterometry reflection profiles used to characterize processing faults on the wafer measured in the scatterometry tool of FIG. 3.
Figure 4B:
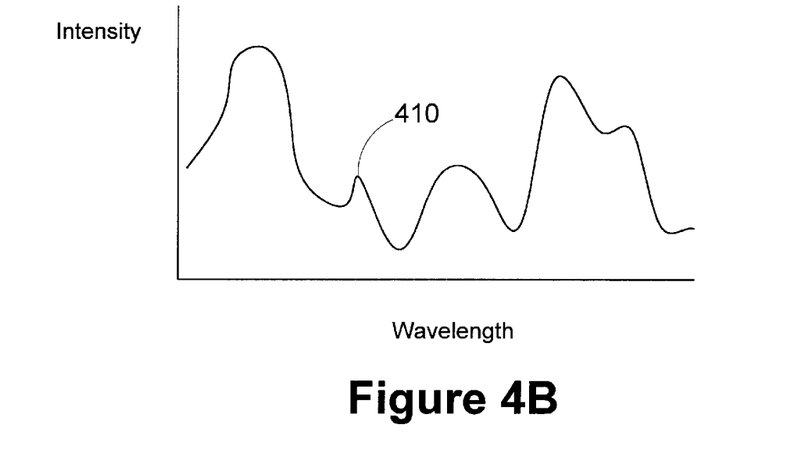
Figure 4C:
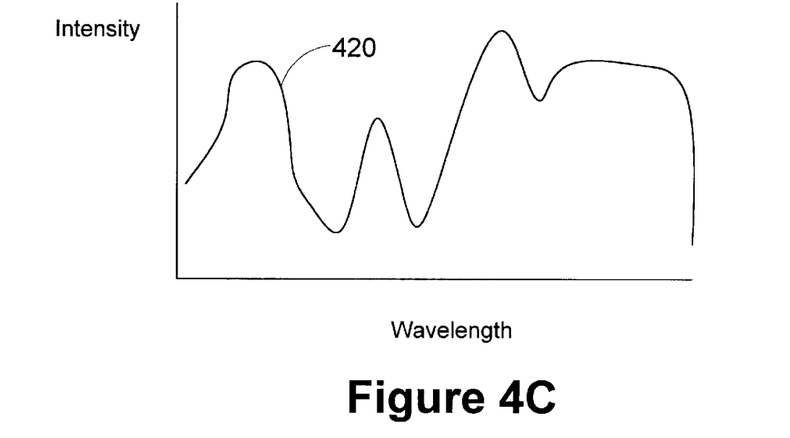

FIGS. 4A, 4B, and 4C illustrate exemplary reflection profiles 400, 410, 420. The reflection profile 400 represents an expected or target reflection profile of the acceptable interconnect structure 200 of FIG. 2A, and may be contained within the fault classification library 132 of FIG. 1. The reflection profiles 410 and 420 of FIGS. 4B and 4C may represent the reflection profiles of the misprocessed interconnect structures 270, 280 of FIGS. 2B and 2C. Many more reflection profiles may be included in the fault classification library 132 for varying undercutting and/or scalloping severity levels.

The data processing unit 138 uses the fault classification library 132 to identify and classify a processing fault with the grating structure 310 by matching the measured reflection profile with one of the misprocessed reflection profiles. Techniques for matching the measured reflection profile to the closest misprocessed reflection profile are well known to those of ordinary skill in the art, so they are not described in greater detail herein. For example, in evaluating the measured reflection profile against the misprocessed reflection profiles in the fault classification library 132, that data processing unit 138 may use a least squared difference technique for determining the closest misprocessed reflection profile.

In another embodiment, the measured reflection profile may be compared to a target reflection profile selected from the fault classification library 132 for an interconnect structure 320 having a known and desired profile. For example, a target reflection profile may be calculated for an interconnect structure 320 having an ideal or acceptable profile using Maxwell's equations, and that target reflection profile may be stored in the fault classification library 132. The reflection profile 400 of FIG. 4A is an exemplary target profile. Thereafter, the measured reflection profile of a grating structure 310 having an unknown interconnect structure profile is compared to the target reflection profile. Based upon this comparison, a relatively rough approximation of the profile may be determined. That is, by comparing the measured reflection profile to the target reflection profile, a significant departure from the expected profile may be identified, such that further matching of the measured reflection profile with additional reference reflection profiles from the fault classification library 132 is unwarranted. Using this technique, an initial determination may be made as to the acceptability of the profile of the interconnect structures 320. Of course, this step may be performed in addition to the matching or correlating of a measured reflection profile to a misprocessed reflection profile from the fault classification library 132 as described above.

Particular techniques for determining the "fit" between the target reflection profile and the measured reflection profile are well known to those of ordinary skill in the art. One exemplary technique includes determining the mean squared distance between the target reflection profile and the measured reflection profile. If the mean squared distance between the measured reflection profile and the target reflection profile is greater than a predetermined threshold, the interconnect structures 320 may be designated as defective, or at least suspect. The specific threshold employed depends on the comparison technique used and the accuracy of the scatterometric measurements.

The scatterometry tool 130 may provide various information regarding the profile of the interconnect structure 320. For example, the scatterometry tool 130 may provide a top width measurement (i.e., the width of the ARC layer 250 and/or hard mask layer 260 and a middle width measurement (i.e., the width of the metal layer 240 at the midpoint of the interconnect structure 320). The difference between these two measurements gives a rough measurement of the amount of undercut. Measurements may also be provided at various heights along the metal layer 240 to characterize the profile of the metal layer 240 (e.g., scalloped). The profile of the metal layer 240 may also be used to estimate its cross-sectional area, thus providing a measurement of the current carrying volume (i.e., when the length of the interconnect line 320 is factored in). The cross-sectional are may be approximated by modeling the metal layer 240 as a plurality of trapezoids determined by the widths measured at various heights by the scatterometry tool 130.

Various thresholds may be used to identify the interconnect structure 320 as being faulty. For example, if the undercut (i.e., difference between top and middle widths) is greater than a predetermined threshold, a fault condition may be identified. In another example, if the cross-sectional area of the metal layer 240 is less than a predetermined threshold, a fault condition may be identified.

Upon identifying a processing fault associated with the interconnect structures 320, the scatterometry tool 130 may send an alert message to an operator of the etch tool 120, a manager of the processing line 100, or to a factory control system 140 (shown in FIG. 1) responsible for controlling the operations of the processing line 100. The factory control system 140 may log the processing fault and schedule the wafer 300 to be scrapped, depending on the specific nature of the misprocessing. The information about the specific type of misprocessing can be used to correct the problem in the etch tool 120 to prevent recurrence.

Figure 5:
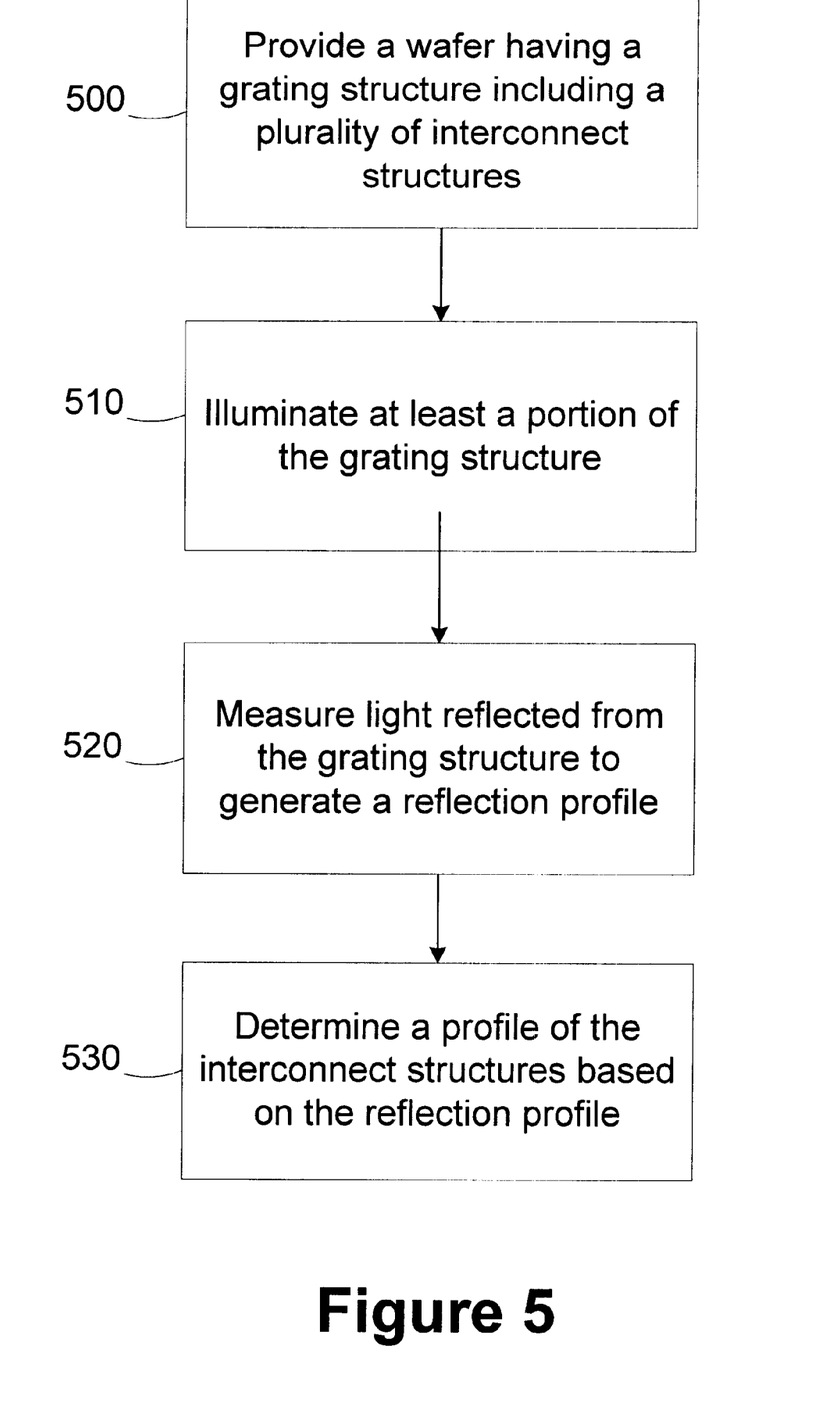
FIG. 5 is a simplified flow diagram of a method for characterizing an interconnect structure profile using scatterometry measurements in accordance with another illustrative embodiment of the present invention.

Turning now to FIG. 5, a simplified flow diagram of a method for characterizing an interconnect structure profile using scatterometry measurements in accordance with another illustrative embodiment of the present invention is provided. In block 500, a wafer having a grating structure including a plurality of interconnect structures is provided. In block 510, at least a portion of the grating structure is illuminated. In block 520, light reflected from the grating structure is measured to generate a reflection profile. In block 530, a profile of the interconnect structures is determined based on the reflection profile.

Detecting and characterizing misprocessed interconnect structures, as described above, allows misprocessed wafers to be identified prior to the expenditure of unnecessary resources required to continue processing the wafer. Such resource conservation improves the efficiency, and thus, the profitability, of the processing line 100. Information about the specific type of misprocessing can be provided to allow correction of the problem in previous process steps to prevent repetitions of the misprocessing.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for characterizing an interconnect structure profile, comprising:

providing a wafer having a grating structure including a plurality of interconnect structures;

illuminating at least a portion of the grating structure;

measuring light reflected from the grating structure to generate a reflection profile; and determining a profile of the interconnect structures based on the reflection profile.

2. The method of claim 1, further comprising identifying a misprocessed condition of the interconnect structures based on the determined profile of the interconnect structures.

3. The method of claim 1, wherein determining the profile of the interconnect structures further comprises:

comparing the generated reflection profile to a fault classification library of reflection profiles, each reference reflection profile having an associated interconnect structure profile;

selecting a reflection profile from the fault classification library closest to the generated reflection profile; and determining the profile of the interconnect structures based on the interconnect structure profile associated with the selected reflection profile.

4. The method of claim 1, wherein generating the reflection profile comprises generating the reflection profile based on at least one of intensity and phase of the reflected light.

5. The method of claim 1, wherein providing the wafer comprises providing the wafer having the grating structure formed in a test structure on the wafer.

6. The method of claim 1, wherein providing the wafer comprises providing the wafer having the grating structure formed in a production device on the wafer.

7. The method of claim 2, wherein identifying the misprocessed condition comprises characterizing the misprocessed condition as an undercut condition.

8. The method of claim 2, wherein characterizing the identifying condition comprises characterizing the misprocessed condition as a scalloped condition.

9. The method of claim 2, wherein the interconnect structures include an aluminum layer, and identifying the misprocessed condition further comprises characterizing a fault in the aluminum layer.

10. The method of claim 1, wherein determining the profile of the interconnect structures further comprises:

comparing the generated reflection profile to a target reflection profile; and determining the profile of the interconnect structures based on the comparison of the generated reflection profile and the target reflection profile.

11. The method of claim 10, further comprising identifying a misprocessed condition of the interconnect structures based on the comparison of the generated reflection profile and the target reflection profile.

12. The method of claim 11, wherein identifying the misprocessed condition of the interconnect structures further comprises identifying the misprocessed condition of the interconnect structures in response to the difference between the measured reflection profile and the target reflection profile being greater than a predetermined threshold.

13. The method of claim 12, wherein comparing the measured reflection profile to the target reflection profile further comprises determining a mean squared distance between the measured reflection profile and the target reflection profile.

14. The method of claim 13, wherein identifying the misprocessed condition of the interconnect structures further comprises identifying the misprocessed condition of the interconnect structures in response to the mean squared distance between the measured reflection profile and the target reflection profile being greater than the predetermined threshold.

15. The method of claim 1, wherein determining the profile of the interconnect structures further comprises determining an undercut measurement.

16. The method of claim 15, further comprising identifying a misprocessed condition of the interconnect structures in response to the undercut measurement being greater than a predetermined threshold.

17. The method of claim 15, wherein determining undercut measurement comprises generating a top width measurement of the interconnect structures and a middle width measurement of the interconnect structures based on the reflection profile and subtracting the middle width measurement from the top width measurement.

18. The method of claim 1, wherein determining the profile of the interconnect structures further comprises determining a cross-sectional area of the interconnect structure.

19. The method of claim 18, further comprising identifying a misprocessed condition of the interconnect structures in response to the cross-sectional area being less than a predetermined threshold.

20. A method for characterizing an interconnect structure profile, comprising:
    providing a wafer having a grating structure including a plurality of interconnect structures;
    illuminating at least a portion of the grating structure;
    measuring light reflected from the grating structure to generate a reflection profile; and
    comparing the generated reflection profile to a fault classification library of reflection profiles, each reference reflection profile having an associated interconnect structure profile;
    selecting a reflection profile from the fault classification library closest to the generated reflection profile; and
    determining a profile of the interconnect structures based on the interconnect structure profile associated with the selected reflection profile.

21. The method of claim 20, further comprising identifying a misprocessed condition of the interconnect structures based on the determined profile of the interconnect structures.

22. The method of claim 20, wherein generating the reflection profile comprises generating the reflection profile based on at least one of intensity and phase of the reflected light.

23. The method of claim 20, wherein providing the wafer comprises providing the wafer having the grating structure formed in a test structure on the wafer.

24. The method of claim 20, wherein providing the wafer comprises providing the wafer having the grating structure formed in a production device on the wafer.

25. The method of claim 21, wherein identifying the misprocessed condition comprises characterizing the misprocessed condition as an undercut condition.

26. The method of claim 21, wherein identifying the misprocessed condition comprises characterizing the misprocessed condition as a scalloped condition.

27. The method of claim 21, wherein the interconnect structures include an aluminum layer, and identifying the misprocessed condition further comprises characterizing a fault in the aluminum layer.

28. The method of claim 20, wherein determining the profile of the interconnect structures further comprises:
    comparing the generated reflection profile to a target reflection profile; and
    determining the profile of the interconnect structures based on the comparison of the generated reflection profile and the target reflection profile.

29. The method of claim 28, further comprising identifying a misprocessed condition of the interconnect structures based on the comparison of the generated reflection profile and the target reflection profile.

30. The method of claim 29, wherein identifying the misprocessed condition of the interconnect structures further comprises identifying the misprocessed condition of the interconnect structures in response to the difference between the measured reflection profile and the target reflection profile being greater than a predetermined threshold.

31. The method of claim 30, wherein comparing the measured reflection profile to the target reflection profile further comprises determining a mean squared distance between the measured reflection profile and the target reflection profile.

32. The method of claim 31, wherein identifying the misprocessed condition of the interconnect structures further comprises identifying the misprocessed condition of the interconnect structures in response to the mean squared distance between the measured reflection profile and the target reflection profile being greater than the predetermined threshold.

33. The method of claim 20, wherein determining the profile of the interconnect structures further comprises determining an undercut measurement.

34. The method of claim 33, further comprising identifying a misprocessed condition of the interconnect structures in response to the undercut measurement being greater than a predetermined threshold.

35. The method of claim 33, wherein determining undercut measurement comprises generating a top width measurement of the interconnect structures and a middle width measurement of the interconnect structures based on the reflection profile and subtracting the middle width measurement from the top width measurement.

36. The method of claim 20, wherein determining the profile of the interconnect structures further comprises determining a cross-sectional area of the interconnect structure.

37. The method of claim 36, further comprising identifying a misprocessed condition of the interconnect structures in response to the cross-sectional area being less than a predetermined threshold.

38. A method for characterizing an interconnect structure profile, comprising:
    providing a wafer having a grating structure including a plurality of interconnect structures;
    illuminating at least a portion of the grating structure;
    measuring light reflected from the grating structure to generate a reflection profile; and
    comparing the generated reflection profile to a target reflection profile; and
    determining a profile of the interconnect structures based on the comparison of the generated reflection profile and the target reflection profile.

39. The method of claim 38, further comprising identifying a misprocessed condition of the interconnect structures based on the determined profile of the interconnect structures.

40. The method of claim 38, wherein generating the reflection profile comprises generating the reflection profile based on at least one of intensity and phase of the reflected light.

41. The method of claim 38, wherein providing the wafer comprises providing the wafer having the grating structure formed in a test structure on the wafer.

42. The method of claim 38, wherein providing the wafer comprises providing the wafer having the grating structure formed in a production device on the wafer.

43. The method of claim 39, wherein identifying the misprocessed condition comprises characterizing the misprocessed condition as an undercut condition.

44. The method of claim 39, wherein identifying the misprocessed condition comprises characterizing the misprocessed condition as a scalloped condition.

45. The method of claim 39, wherein the interconnect structures include an aluminum layer, and identifying the misprocessed condition further comprises characterizing a fault in the aluminum layer.

46. The method of claim 39, wherein identifying the misprocessed condition of the interconnect structures further comprises identifying the misprocessed condition of the interconnect structures in response to the difference between the measured reflection profile and the target reflection profile being greater than a predetermined threshold.

47. The method of claim 46, wherein comparing the measured reflection profile to the target reflection profile further comprises determining a mean squared distance between the measured reflection profile and the target reflection profile.

48. The method of claim 47, wherein identifying the misprocessed condition of the interconnect structures further comprises identifying the misprocessed condition of the interconnect structures in response to the mean squared distance between the measured reflection profile and the target reflection profile being greater than the predetermined threshold.

49. The method of claim 38, wherein determining the profile of the interconnect structures further comprises determining an undercut measurement.

50. The method of claim 49, further comprising identifying a misprocessed condition of the interconnect structures in response to the undercut measurement being greater than a predetermined threshold.

51. The method of claim 49, wherein determining undercut measurement comprises generating a top width measurement of the interconnect structures and a middle width measurement of the interconnect structures based on the reflection profile and subtracting the middle width measurement from the top width measurement.

52. The method of claim 38, wherein determining the profile of the interconnect structures further comprises determining a cross-sectional area of the interconnect structure.

53. The method of claim 52, further comprising identifying a misprocessed condition of the interconnect structures in response to the cross-sectional area being less than a predetermined threshold.

\* \* \* \* \*